United States Patent
Maner et al.

(10) Patent No.: US 6,835,854 B1
(45) Date of Patent: Dec. 28, 2004

(54) PROCESS FOR THE PREPARATION OF HIGH QUALITY 3,3',4,4'-TETRAMINOBIPHENYL

(75) Inventors: Asif Maner, Pune (IN); Sudhir Bavikar, Pune (IN); Arumugam Sudalai, Pune (IN); Swaminathan Sivaram, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/804,886

(22) Filed: Mar. 19, 2004

Related U.S. Application Data

(63) Continuation of application No. PCT/IN03/00403, filed on Dec. 29, 2003.

(51) Int. Cl.[7] .............................................. C07C 211/00
(52) U.S. Cl. ....................................................... 564/309
(58) Field of Search ........................................ 564/309

(56) References Cited

U.S. PATENT DOCUMENTS

| | | | | |
|---|---|---|---|---|
| 3,686,149 A | * | 8/1972 | Ohfuji | 528/342 |
| 3,865,876 A | * | 2/1975 | Chenevey et al. | 564/407 |
| 3,943,175 A | * | 3/1976 | Druin et al. | 564/309 |
| 4,433,168 A | * | 2/1984 | Schubert et al. | 564/309 |
| 5,235,105 A | * | 8/1993 | Vorwerk | 564/309 |

FOREIGN PATENT DOCUMENTS

| | | | |
|---|---|---|---|
| JP | 49011212 | * | 5/1970 |
| JP | 49011213 | * | 5/1970 |
| JP | 60158146 | * | 1/1984 |

* cited by examiner

*Primary Examiner*—Samuel Barts
(74) *Attorney, Agent, or Firm*—Baker Botts L.L.P.

(57) ABSTRACT

The present invention relates to a process for the preparation of pure high quality 3,3', 4,4'-tetraminobiphenyl (TAB) in high yields. The present invention also discloses a process for the preparation of 3,3',4,4' tetraminobiphenyl (TAB) comprising a three step process: (1) oxidation 3,3'-dichloro 4,4'-diaminobiphenyl (DCB) with 50% aq. $H_2O_2$, (2) ammonolysis of the resulting 3,3'-dinitro 4,4'-dinitrobiphenyl (DCDNB) and (3) reduction of 3,3'-diamino-4,4'-dinitrobiphenyl (DADNB) with stannous chloride and concentrated hydrochloric acid.

10 Claims, No Drawings

PROCESS FOR THE PREPARATION OF HIGH QUALITY 3,3',4,4'-TETRAMINOBIPHENYL

CROSS-REFERENCE TO RELATED APPLICATIONS

This is a continuation of International Application No. PCT/IN2003/00403, filed Dec. 29, 2003, which is incorporated by reference herein in its entirety.

FIELD OF THE INVENTION

The present invention relates to a process for the preparation of pure high quality 3,3', 4,4'-tetraminobiphenyl (TAB) of formula 1 in high yields.

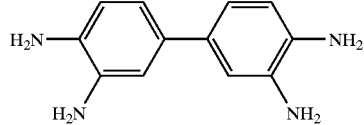

FORMULA-1

BACKGROUND OF THE INVENTION 3,3',4,4'-Tetraminobiphenyl (TAB) is a valuable intermediate and final product in various areas. For example, TAB is used as monomer in the preparation of polybenzimidazole (PBI) polymers, which are characterized by excellent thermal and mechanical stability. These PBI polymers are widely used as proton-conducting materials for fuel cell applications (compare U.S. Pat. Nos. 2,895,948, 3,174,947, 5,317,078 and 6,187,231). TAB is also used as an antioxidant and as an agent for stabilizing epoxide resins.

In the prior art, TAB has been prepared by three known methods. One such known method is ammonolysis of 3,3'-dichlorobenzidine (DCB) in the presence of mainly Cu catalysts, including both copper salts and elemental Cu, using aqueous $NH_3$. For example, French Patent Specification No. 1,475,631 describes such an ammonolysis of DCB, in the presence of a CuI salt and/or of $Cu_2O$ and $CaCl_2$, at an elevated temperature, preferably 150–210° C. and under an elevated inert gas pressure. The crude TAB thus obtained is purified via its salt formation with a strong acid. The yield of TAB is about 70%. Subsequently, various attempts have been made to obtain TAB in highly pure form and in high yields from crude TAB as described below.

U.S. Pat. No. 3,865,876 describes an improvement on the result of the method described in French Patent Specification No. 1,475,631 by using essentially only CuCl as a catalyst for the ammonolysis of DCB. The yield of TAB of theory having purity of about 75–82% is between about 85 and 87%. This product has a Cu content of about 3–6% by weight.

U.S. Pat. No. 3,943,175 discloses the use of CuCl and Cu powder as a catalyst. It also describes the purification of TAB by using of sulfuric acid, converting it to sulfate, isolation of the sulfate and liberation therefrom of TAB by means of a base. The TAB thus liberated is dissolved and reprecipitated from an aqueous solution advantageously with the addition of activated charcoal and diatomaceous earth. However, the Cu content present in TAB is about 0.6 to 0.9% and the yield at most 45.7% of theory, relative to DCB employed.

German Patent DE 3,111,470 discloses the purification of crude TAB obtained by ammonolysis process by boiling it with $H_2O$ containing activated carbon and sodium dithionate. The yield of TAB using the disclosed process is 75.9% with ≦0.0005% Cu content.

Japanese Patent No. 60,158,146 also describes the purification of TAB by refluxing the crude TAB with activated charcoal, aqueous $FeCl_3$ solution and hydrazide hydrate. The yield of TAB using the disclosed process is 83.2% containing ≧10 ppm Cu.

The purification of crude TAB obtained from ammonolysis of DCB with copper catalyst by crystallizing it in water in presence of 0–5% by weight of activated carbon and about 1–2% by weight of a water-soluble reducing agent, i.e. alkali metal dithionate or alkali metal sulfite, at temperature of 100–140° C. under $N_2$ atmosphere has been disclosed. (U.S. Pat. Nos. 4,433,168, 5,235,105 and Eur. Pat. Appl. EP 522,577). The yield of TAB using the disclosed process is 88.2% of theory with only 10 ppm Cu).

In a second method for producing TAB, which has generated substantial interest, the starting material is benzidine which is acetylated with acetic anhydride, to form N,N-diacetylbenzidine. The latter compound is then nitrated with conc. $HNO_3$ to form 3,3'-dinitro-N, N-diacetylbenzidine which is base hydrolyzed to form 3.3'-dinitrobenzidine. This is then reduced by any of various means to form TAB (H. Vogel and C. S. Marvel, J. Poly. Sci. Part Al, 1531 (1963)).

In a third method for the production of TAB, biphenyl is used as the starting material. The method comprises the following six steps: (1) acetylating the biphenyl in the presence of an appropriate Friedel—Crafts catalyst to obtain 4,4'-diacetylbiphenyl (DAcB); (2) oximating the DAcB to form DAcB dioxime; (3) subjecting the dioxime to a double Beckmann rearrangement to obtain N,N'-diacetylbenzidine (DiAcBz); (4) nitrating the DiAcBz to obtain 3,3'-dinitro-N,N'-diacetylbenzidine (DNAcBz); (5) removing the acetyl groups of the DNAcBz by basic hydrolysis to form 3,3'-dinitrobenzidine (DNB) and (6) reducing the nitro groups of DNB to form TAB (U.S. Pat. No. 5,041,666).

There are various disadvantages associated with the foregoing methods. The use of benzidine, for example, as one of the raw materials, is undesired since it is a known carcinogen.

Direct ammonolysis of DCB catalyzed by copper salts also requires high temperatures (200°–300° C.) at a pressure of 900–1000 psig, which causes the manufacturing process to be hazardous. The use of such harsh reaction conditions is undesired.

Direct ammonolysis of DCB as disclosed by the prior art methods generates tarry materials, which always accompany the TAB produced.

Direct ammonolysis also causes the formation of stable complexes, where copper is likely complexed with TAB in situ, requiring the extraction of TAB from the complex. Furthermore, direct ammonolysis also causes the formation of other stable complexes, where copper is likely complexed with the corresponding triaminobiphenyl. This impurity must also be removed during the manufacturing process.

Lastly, the prior art methods utilize relatively expensive starting materials. Thus, any method for producing TAB utilizing a cheaper raw material, which is both safer and easier to handle, would be very desirable.

The main object of the present invention is to provide an improved process for the preparation of pure high quality 3,3,'4,4'-tetramino biphenyl (TAB), which avoids the drawbacks as discussed above.

Another object of the present invention is to provide for the use of heterogeneous Ti-superoxide as a catalyst for the oxidation of DCB to obtain 3,3'-dichloro-4,4'-dinitrobiphenyl (DCDNB). DCDNB which smoothly underwent ammonolysis affording 3,3'-dichloro-4, 4'dinitrobiphenyl (DADNB), followed by the reduction of nitro groups of DADNB yielded TAB in high yields.

Yet another object is to provide a novel process for the synthesis of TAB of greater purity than then achieved using the methods disclosed by the prior art.

SUMMARY OF THE INVENTION

The present invention relates to a process for the preparation of pure high quality 3,3', 4,4'-tetraminobiphenyl (TAB) in high yields.

More particularly, it relates to a process for preparation of 3,3',4,4' tetraminobiphenyl (TAB) involving a three step process comprising (1) oxidation of 3,3'-dichloro 4,4'-diaminobiphenyl (DCB) with 50% aqueous $H_2O_2$, (2) ammonolysis of the resulting 3,3'-dinitro 4,4'-dinitrobiphenyl (DCDNB) and (3) the reduction of 3,3'-diamino-4,4'-dinitrobiphenyl (DADNB) with stannous chloride and concentrated hydrochloric acid.

DETAILED DESCRIPTION OF THE INVENTION

The present invention provides an improved process for the preparation of pure, high quality 3,3',4,4'-Tetraminobiphenyl(TAB) of formula 1

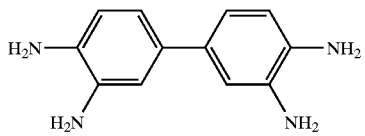

FORMULA-1 from 3,3'-Dichloro benzidine (DCB) of formula 2

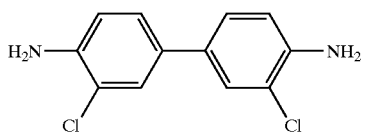

FORMULA-2 which comprises (a) oxidizing DCB by using an oxidizing agent in the presence of a Titanium superoxide catalyst, in the presence of a solvent to obtain 3,3'dichloro 4,4'dinitro biphenyl (DCDNB) of formula 3;

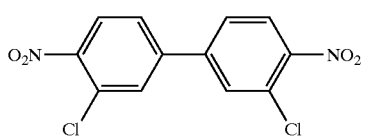

FORMULA-3

(b) ammonolyzing DCDNB using aqueous ammonia in presence of a solvent to obtain 3,3',diamino 4,4' dinitro biphenyl (DADNB) of formula 4;

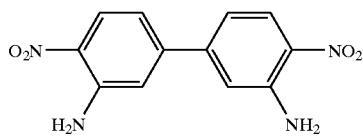

FORMULA-4

(c) reducing DADNB using a reducing agent; and (d) making basic the resultant mixture with an alkali to obtain 3,3',4,4' tetraminobiphenyl (TAB).

In one embodiment of the present invention, the titanium superoxide used as the heterogeneous catalyst is prepared as discussed in Angew. Chem. Int. Ed. Engl. 2001,40,405–408.

In another embodiment of the present invention, the oxidant may be preferably $H_2O_2$ at a concentration of 30 to 50% v/v.

In yet another embodiment of the present invention, the solvent used may be selected from a range of organic solvents, such as, but are not limited to, acetonitrile, acetone methanol, acetic acid and water.

In yet another embodiment of the present invention, ammonolysis may be carried out at temperature ranging from 50–200° C., preferably 100° C.

In yet another embodiment of the present invention, ammonolysis may be carried out at a pressure of 100–500 psig, preferably 100 psig.

In yet another embodiment of the present invention, the reducing agent is selected from a group consisting of $SnCl_2$/conc. HCl mixture.

In yet another embodiment of the present invention, reduction is carried out at in the temperature ranging between 50–60° C.

EXAMPLES

Example 1

Preparation of Ti-superoxide catalyst (1)

To a solution of Ti $(O^1Pr)_4$, (5.0 g, 0.0175 moles) in anhydrous MeOH (50 mL) placed in a two-necked round bottomed flask equipped with addition funnel, nitrogen inlet and reflux condenser, 50% $H_2O_2$, (5.98 g, 0.175 moles) was added slowly over a period of 40 minutes while stirring at room temperature. The yellow-colored precipitate formed at once was filtered through a sintered funnel, washed with anhydrous methanol and dried under reduced pressure (3 mm Hg) at room temperature (25° C.) for 1 h, Yield: 3.94 g (98%). EPR spectra were recorded on a Bruker EMX spectrometer operating at 9.76 GHz, 298 K and g values were determined with reference to standard marker: α, α'-diphenyl-β-picryl hydrazyl (DPPH, g=2.0036). Thermogravimetric and differential thermal analysis (TG/DTA) was performed on TG/DTA 22, TG/DTA 32 system (Seiko Instruments Inc.) in the range of 30–400° C. with a temperature program 10° C./min.

Example 2

Preparation of 3,3'-dichloro-4,4'-dinitrobiphenyl (DCDNB) by oxidative Procedure In a two-necked round-bottomed flask equipped with nitrogen gas bubbler, addition funnel, water condenser and stirring magnetic bar were placed 3,3'-dichlorobenzidiene (5 g, 0.019 moles), Ti-superoxide catalyst (1), (2.5 g, 50 wt %) and anhydrous methanol (30 ml). 50% aq. $H_2O_2$, (10.74 g, 0.158 moles) was added slowly under stirring for a period of 20 min. Reaction was found to be exothermic and a yellow to reddish brown color change was observed during the addition of $H_2O_2$. The progress of the reaction was monitored by TLC in ethyl acetate and after completion, catalyst 1 was filtered out and methanol evaporated under reduced pressure. The crude product weighed 4.2 g, (66.28%) was analyzed by gas chromatography for its purity.

Example 3

Preparation of 3,3'-diamino 4,4'dinitrobiphenyl (DADNB) by ammonolysis Procedure A mixture of 3,3'-dichloro-4,4'-dinitrobiphenyl (5 g, 0.0197 mol) and excess ammonia solution (100 ml), in methanol (100 ml) was charged into an autoclave and the whole mixture was heated at 100° C. for 3h. After the reaction was complete, methanol was removed by distillation and the amino product was precipitated. It was then filtered and washed with $H_2O$ and dried. Yield 3.82 g (86.99%) m.p. 226° C.

Example 4

Preparation of 3,3'-4,4'-tetraminobiphenyl (TAB) by Reduction of nitro Groups A mixture of 3,3'-dinitrobenzidine (2 g, 0.007 mol) and stannous chloride (6.4 g, 0.034 mol) was stirred at 0° C. in ethanol (125 ml) and con. HCl (30%) was added drop-wise over 30 min. The reaction mixture was refluxed for 10–12 h. The salt of the tetramine was precipitated out, which was made basic with cold 10% NaOH solution and the solid filtered out, washed with water dried under vacuum to give TAB in 80% yield (1.159 g).

The advantages of the present invention are:
1. In all three steps of reactions, the isolation of the products can be done by simple filtration.
2. The ammonolysis of DCB can be done without the use of any metal catalyst and under milder reaction temperature (100° C.) and autogenic pressure (250 psig).
3. The product TAB can be produced without any contamination of copper and its salts, thus enhancing the purity of TAB.
4. No by-products, e.g. diamine complexes of TAB with copper salts, are produced in the reaction mixture.
5. Quantitative conversions are obtained in all the three steps of oxidation, ammonolysis, and reduction.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims. Various references are cited herein, the disclosure of which are incorporated by reference in their entireties.

We claim:
1. A process for preparing 3,3',4,4'-Tetraminobiphenyl (TAB) of formula 1 comprising

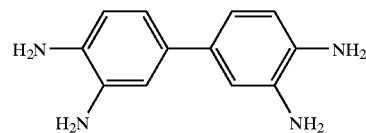

FORMULA-1 a. oxidizing 3,3' dichloro benzidine of formula 2 with an oxidizing agent in the presence of a titanium superoxide catalyst and a solvent to obtain a 3,3' dichloro 4,4' dinitro biphenyl of formula 3;

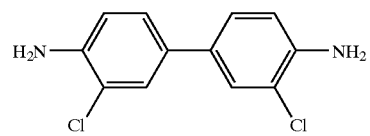

FORMULA-2

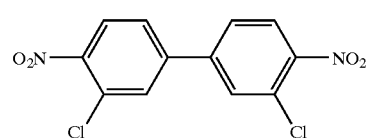

FORMULA-3 b. ammonolyzing the 3,3' dichloro 4,4' dinitro biphenyl of formula 3 with ammonia in the presence of a solvent to obtain a 3,3' diamino 4,4' dinitro biphenyl of formula 4;

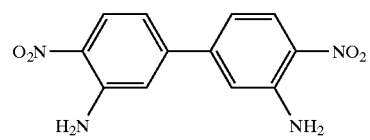

FORMULA-4 c. reducing the 3,3', diamino 4,4' dinitro biphenyl of formula 4 with a reducing agent; and
d. treating the reduced product of step c with an alkali to obtain the 3,3',4,4' tetraminobiphenyl of formula 1.

2. The process of claim 1, wherein the titanium superoxide catalyst is a heterogeneous catalyst.

3. The process of claim 1, wherein the oxidizing agent is $H_2O_2$ at a concentration of 30 to 50% v/v.

4. The process of claim 1, wherein the solvent is selected from the group consisting of acetonitrile, acetone, methanol, acetic acid, and water.

5. The process of claim 1, wherein ammonolysis is performed at a temperature ranging between 50–200° C.

6. The process of claim 1, wherein ammonolysis is performed at a temperature of 100° C.

7. The process of claim 1, wherein ammonolysis is performed at a pressure ranging between 100–500 psig.

8. The process of claim 1, wherein ammonolysis is performed at a pressure of 100 psig.

9. The process of claim 1, wherein the reducing agent is a $SnCl_2$/concentrated HCl mixture.

10. The process of claim 1, wherein reduction is performed at a temperature ranging between 50–60° C.

* * * * *